United States Patent [19]

Abend et al.

[11] 4,011,273

[45] Mar. 8, 1977

[54] METHOD FOR THE PRODUCTION OF GUERBET ALCOHOLS UTILIZING INSOLUBLE LEAD CATALYSTS

[75] Inventors: Phillip Gary Abend, Teaneck; Peter Leenders, Allendale, both of N.J.

[73] Assignee: Henkel Inc., Teaneck, N.J.

[22] Filed: Aug. 4, 1975

[21] Appl. No.: 601,371

[52] U.S. Cl. .......................... 260/642 C; 252/461; 260/617 R; 260/618 R

[51] Int. Cl.² ........................................ C07C 29/00

[58] Field of Search ....... 260/642 C, 617 R, 618 R; 252/461

[56] References Cited

UNITED STATES PATENTS

| | | | |
|---|---|---|---|
| 2,050,789 | 8/1936 | Fuchs et al. | 260/642 C |
| 2,836,628 | 3/1958 | Miller | 260/642 C |
| 3,119,880 | 1/1964 | Kollar et al. | 260/642 C |
| 3,558,716 | 1/1971 | Engelhardt | 260/642 C |

*Primary Examiner*—James O. Thomas, Jr.
*Assistant Examiner*—James H. Reamer
*Attorney, Agent, or Firm*—Hammond & Littell

[57] ABSTRACT

An improvement in the production of Guerbet alcohols by the condensation of alcohols in the presence of a catalyst and an alkali consisting of utilizing from 0.05 to 3.0 gm per mol of total alcohol of an insoluble lead salt of an oxyacid of a group IV element having a molecular weight greater than 27, such as oxyacids selected from the group consisting of the silicate, the titanate, the zirconate, the germanate and the hafnate, as said catalyst.

6 Claims, No Drawings

METHOD FOR THE PRODUCTION OF GUERBET ALCOHOLS UTILIZING INSOLUBLE LEAD CATALYSTS

THE PRIOR ART

According to the Guerbet reaction, α-branched primary alcohols are obtained by reacting primary alcohols having a methylene in the α-position in the presence of an alkali and at elevated temperatures according to the following reaction

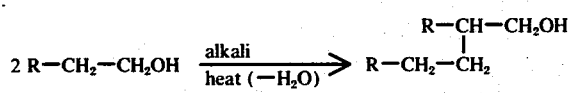

The Guerbet alcohol produced has twice as many carbon atoms as the starting alcohol. This reaction has been known for years, however side reactions and incomplete reactions readily occur. In view thereof the prior art workers have experimented with many types of reaction conditions to improve the performance of the reaction. Various types of condensation catalysts and dehydrogenation catalysts have been employed.

For example in U.S. Pat. No. 3,119,880, patentee describes the Guerbet reaction in the presence of an alkali, a lead salt at least partially soluble in the reactant alcohol and, optionally a nickel dehydrogenation catalyst. Patentee employes various lead salts such as the nitrate, acetate, octanoate, naphthenate, perchlorate, β-naphthalene sulfonate, oleate, phenolsulfonate, stearate, etc. Lead acetate trihydrate is the preferred salt. However, in the absence of the nickel dehydrogenation catalyst patentee indicates that both conversions and yields are down. In addition the amount of soluble lead salt is critical to good yields and amounts of 0.5 gm per mol of alcohol gave poor yields.

In U.S. Pat. No. 3,558,716, patentee describes the Guerbet reaction in the presence of dehydrogenation catalyst such as an oxide of copper, zinc, lead, chromium, molybdenum, tungsten and manganese, basically activated by a basic substance are such as zinc oxide, cadmium oxide and the oxides and hydroxides of alkali metals and alkaline earth metals. When the catalyst is employed in amounts of 5 gm per mol of alcohol, the Guerbet alcohol is converted into the corresponding aldehyde. Here, the basic activation of the dehydrogenation catalyst forms reaction soluble components which are difficult to recover for recycling. Moreover if lead oxides are employed they tend to be deactivated when sintered to reuse and form hard balls with low surface area.

OBJECTS OF THE INVENTION

An object of the present invention is the development of a process for the condensation of alcohols by the Guerbet process under alkaline conditions employing an insoluble catalyst which is stable under the reaction conditions and gives high conversions and high yields.

Another object of the present invention is the development in the process for the condensation of alcohols by the Guerbet process for the production of branched alcohols having the formula $$R_2-CH_2-CH_2-\underset{\underset{R_1}{|}}{C}H-CH_2-OH$$

wherein $R_2$ and $R_1$ are members having from 2 to 20 carbon atoms selected from the group consisting of alkyl, alkenyl, alkynyl, cycloalkyl alkyl, phenylalkyl and alkylphenylalkyl comprising condensing an alcohol having the formula $$R_2-CH_2-CH_2OH$$

with an alcohol having the formula $$R_1-CH_2-CH_2OH$$

wherein $R_2$ and $R_1$ have the above assigned values in the presence of an alkali under substantially anhydrous reaction conditions in the presence of a catalyst at temperatures above 100° C to the reflux temperature, and recovering said branched alcohols, the improvement consisting of conducting said condensation in the presence of from 0.05 to 3.0 gm per mol of total alcohol, of an insoluble lead salt of an oxyacid of a group IV element of the Periodic Table having a molecular weight greater than 27, as said sole catalyst.

These and other objects of the invention will become more apparent as the description thereof proceeds.

DESCRIPTION OF THE INVENTION

The drawbacks of the prior art have been overcome and the above objects have been achieved by the discovery of novel lead catalysts for the condensation of alcohols according to the Guerbet process. The novel lead catalysts of the inventive process are insoluble lead salts of oxyacids of a group IV element of the Periodic Table having a molecular weight greater than 27, such as the lead silicates, the lead titanates, the lead zirconates, the lead germanates and the lead hafnates. These lead salts can have varying ratios of lead monooxide to $MeO_2$ where Me is a group IV element having a molecular weight greater than 27, such as silicon, titanium, zirconium, germanium and hafnium, and varying degrees of basicity. It is preferred to employ from 0.05 to 3.0 gm, particularly from 0.15 to 1.5 gm, of the insoluble lead catalyst per mol of total alcohols being condensed. Excellent yields and conversions are obtained by the use of these insoluble lead catalysts without the requirement of additional dehydrogenation catalysts or basic activators being employed.

The invention therefore comprises, in the process for the condensation of alcohols by the Guerbet process for the production of branched alcohols having the formula $$R_2-CH_2-CH_2-\underset{\underset{R_1}{|}}{C}H-CH_2OH$$

wherein $R_2$ and $R_1$ are members having from 2 to 20 carbon atoms selected from the group consisting of alkyl, alkenyl, alkynyl, cycloalkyl alkyl, phenylalkyl and alkylphenylalkyl comprising condensing an alcohol having the formula $$R_2-CH_2-CH_2OH$$

with an alcohol having the formula $$R_1-CH_2-CH_2OH$$

wherein $R_2$ and $R_1$ have the above assigned values in the presence of an alkali under substantially anhydrous reaction conditions in the presence of a catalyst at temperatures above 100° C to the reflux termperature, and recovering said branched alcohols, the improvement consisting of conducting said condensation in the presence of from 0.05 to 3.0 gm per mol of total alcohol, of an insoluble lead salt of an oxyacid of a group IV element of the Periodic Table having a molecular weight greater than 27, as said sole catalyst.

Preferably the lead catalyst employed is one of the lead silicates. The lead silicates are compounds, minerals and fused homogeneous mixtures in which the ratio of lead monooxide (PbO) to silicon dioxide ($SiO_2$) can vary from 65% PbO to 90% by weight based on the weight of PbO + $SiO_2$ in the compound. The lead silicates can contain hydroxyl groups but other elements are present only in very minor amounts as impurities. Among the preferred lead silicates are lead metasilicate ($PbSiO_3$), dilead orthosilicate ($Pb_2Si_2O_7$) and basic silicate white lead.

It was noted that when other lead catalysts were utilized, such as lead monooxide, lead oxides, lead carbonate or a lead ion exchanged molecular sieve (a synthetic aluminosilicate with lead ions), in the Guerbet synthesis, the catalysts undergo a physical breakdown of the catalyst structure and lower conversions and yields of the Guerbet alcohols are obtained. The lead oxides tend to agglomerate under the reaction conditions and block the reactor outlets and cannot readily be recycled. Lead carbonate is not stable in the alkaline media of the reaction and breaks down to lead oxides. The lead ion exchanged molecular sieves also tend to break down under the reaction conditions and deposit silicate scale on the stirrer and reaction vessel walls. However, the lead catalysts used in the invention are remarkably stable physically and give excellent conversions and yields. Moreover when recycled, they are readily reactivated by sintering without change of their physical structure.

All primary alcohols which have an α-methylene group may be used as the starting material for producing the α-branched primary alcohols by the Guerbet process. The alcohols may be straight-chained or branched-chained, saturated or unsaturated, cycloaliphatic, substituted with aromatic or heterocyclic rings or even contain hetero atoms which do not interfer during the reaction. The number of carbon atoms in the alcohols is preferably from 4 to 22. Ordinarily, one alcohol is employed as the starting material. However two or more different alcohols may be employed, in which case at least one half of the total mols of alcohol must be free of an α substituent. The starting alcohols need not be 100% primary alcohols free of an α substituent. It has also been found that a recycled purified reaction product to which additional starting alcohols have been added, which material contains 30 to 40% dimeric Guerbet alcohols, may be employed.

Preferably the starting alcohols have the formulae $$R_2-CH_2-CH_2OH$$

and $$R_1-CH_2-CH_2OH$$

wherein $R_2$ and $R_1$ may be the same or different members having from 2 to 20 carbon atoms selected from the group consisting of alkyl, alkenyl, alkynyl, cycloalkylalkyl, phenylalkyl and alkylphenylalkyl. Among such alcohols are n-butyl alcohol, n-amyl alcohol, isoamyl alcohol, n-octanol, n-decanol, lauryl alcohol, stearyl alcohol, oleyl alcohol, phenylstearyl alcohol, 3-butenol-1, linoleyl alcohol, 3-pentynol-1, 4-cyclohexylbutenol-1, 3-phenyl-propanol-1, etc.

The alkali employed in the process can be of an alkali metal or an alkali metal hydroxide including the hydroxides of lithium, sodium, potassium, rubidium and cesium and mixtures thereof. The amount of alkali employed is a function of the amount of alcohol employed as charge stock. However, with the use of the insoluble lead catalysts, the amount of alkali required in the reaction can be reduced considerably over that customarily employed. The molar ratio of alkali to alcohol should be from 0.01 to 0.5 mol, preferably 0.033 to 0.2 mol, per mol of alcohol. Preferably the alkali employed is an aqueous concentrated alkali metal hydroxide such as a 45% aqueous solution of KOH or NaOH.

The optimum temperature employed in the process of the invention will vary with the alcohol charged. Generally, the present process can be carried out effectively at the reflux temperature of the alcohol being treated. While a temperature as low as about 80° C can be used and satisfactory results will be obtained, it is preferred to employ a temperature of at least about 100° C at atmospheric pressure in order to remove the water of reaction substantially as fast as it is formed. Such removal of water is beneficial for high conversions and yields. The upper temperature limit is the temperature at which thermal breakdown of the alcohol charge or product begins to occur. This limit is generally about 350° to about 400° C. In general, however, a refluxing temperature of about 150° to about 240° C at the autogenous pressure of the reactant mixture is considered most satisfactory. In the process of the invention, using the insoluble lead catalysts, a further advantage is that the reaction can be conducted at lower temperatures then ordinarily employed, such as from 80° C to the reflux temperature.

Generally, the present process can be carried out effectively at atmospheric pressure. However, if the boiling point of the alcohol being treated is below the optimum reaction temperature, the reaction can be carried out in a confined system in which case a pressure as high as about 250 pounds per square inch gauge, preferably no higher than about 100 pounds per square inch gauge, can be used. In any event, the pressure should be sufficient to keep the reactants in the liquid phase. If the reaction is carried out at an elevated pressure in a confined system care should be exercised to remove from the reaction area substantially all of the water formed during the course of the reaction in order to obtain desired high conversions and yields.

The time required for the reaction is not particularly critical and can be varied as desired although it should be sufficiently long to insure obtaining an appreciable conversion of the alcohol to the dimer product but not so long as to allow further condensation to form trimers and tetramers. In general, a reflux time of about 5 minutes to about 24 hours or more is adequate although best results are obtained with a period of about 0.5 to about 3 hours at optimum temperatures, pressure, and catalyst concentration.

The following specific embodiments are illustrative of the practice of the invention without being limitative in any respect.

EXAMPLE 1

Preparation of Lead Metasilicate

Lead nitrate, 0.05 mol, 16.5 gm was dissolved in 200 ml of water.

Sodium metasilicate (anhydrous), 0.05 mol, 6.1 gm was dissolved in 200 ml of water.

The lead nitrate solution was slowly added to the sodium metasilicate solution with vigorous stirring forming a white precipitate. This precipitate was filtered. The filter cake was washed with 500 ml of water then dried in an oven at 240° C for 2 hours. This product, lead metasilicate, $PbSiO_3$, was utilized in the following examples as indicated.

EXAMPLE 2

Preparation of 2-Hexyldecanol

A typical preparation of 2-hexyldecanol by the Guerbet condensation of n-octanol-1 is as follows:

APPARATUS

A 500 ml stainless steel 3 neck round bottom flask was employed, fitted with a stainless steel stirrer, a thermometer attached to an electronic temperature regulator and a 65 ml Dean-Stark watr separator that has a reflux condenser attached to it. Heating is by means of an electrically operated heating mantle.

CHARGE

Into the flask were charged:

| | | |
|---|---|---|
| Octanol-1 ("Alfol 8" Conoco Chemicals) | 2.0 mols | (260 gm) |
| KOH (45% aqueous solution) | 0.2 mols | ( 25 gm) |
| Basic Silicate White Lead 202 Micronized | | |
| (Eagle-Picher Industries) | | 0.70 gm |
| The Dean-Stark water separator was filled with 65 ml of Octanol-1. | | |

PROCEDURE

With rapid agitation the contents of the flask were heatd to a set temperature, regulated by the electronic temperature regulator, of 220° C. After 70 minutes to reaction mixture had begun to reflux (187° C). After an additional 130 minutes, the temperature of the reaction mixture had reached 220° C, and a total of 30 ml of water had distilled over into the Dean-Stark water separator.

The reactor was cooled to 60° C and the contents poured into a steam heated separatory funnel fitted with a thermometer and a mechanical stirrer. The organic phase was washed successively with four 400 ml portions of 6% sodium chloride solution.

The separated organic phase was dried by distillation at 40 mm Hg (water jet aspirator pump) and a maximum pot temperature of 110° C.

The water aspirator was then replaced by a mechanical vacuum pump. All volatile material was distilled off at a maximum pot temperature of 185° C and a vacuum of 1.5 mm Hg. 226 gm of distillate was collected. It showed the following composition by Gas-Liquid Chromatographic Analysis:

| | |
|---|---|
| Octanol-1 | 22.23% |
| Unsaturated C-16 alcohol | 0.75% |
| 2-hexyldecanol-1 | 75.75% |
| Total Saturated and Unsaturated $C_{24}$ | 1.28% |

A residue weight of 18.2gm was obtained. These data correspond to an 81.8% conversion of octanol-1 (counting the 30 ml of octanol-1 in the Dean-Stark water separator that flowed back into the reactor) and a yield of 82.5% of 2-hexyldecanol based on reacted octanol-1. The aqueous washings were acidified with 25 gm of sulfamic acid and then extracted with 2,500 ml portions of ethyl ether. Evaporation of the ether yielded 9 gm of octanoic acid.

EXAMPLE 3

Example 2 was repeated but with the same molar amount (0.76 gm) of lead metasilicate ($PbSiO_3$), in place of the basic silicate white lead as sole catalyst. The process was identical except that the final reaction temperature of 220° C was maintained for 15 minutes after this temperature was reached.

2-Hexyldecanol-1 was obtained with a conversion of 85.7% and a yield of 84.1%, being a better yield than that obtained in Example 2.

However, for economic reasons, the use of the commercially available basic silicate white lead is preferred as a lead catalyst.

EXAMPLE 4 (COMPARISON)

When the conditions of Example 2 were repeated substituting 1.67 gm of Harshaw Catalyst 1106-P, a barium oxide promoted copper chromite, for the Basic Silicate White Lead 202 Micronized, the remainder of the experimental conditions being duplicated, except that the time of heating from the reflux temperature to 220° C was 30 minutes under the same heating conditions, a conversion of 87% and a yield of 65% of 2-hexyldecanol-1 were obtained.

EXAMPLE 5 (COMPARISON)

When the conditions of Example 2 were repeated substituting 4.3 gm of Girdler Catalyst G-49A, a nickel on Kieselguhr catalyst, the remainder of the experimental conditions being duplicated, a conversion of 63% and a yield of 75% of 2-hexyldecanol-1 were obtained.

These last two examples indicate the criticality of the use of the insoluble lead catalysts in the Guerbet condensation.

EXAMPLE 6

Preparation of 2-octyldodecanol-1

The apparatus employed in Example 2 was likewise employed in this example.

CHARGE

Into the flask were charged:

| | |
|---|---|
| Decanol-1 | 2 mols (318 gm) |
| KOH (45% aqueous solution) | 0.1 mol (12.5 gm) |
| PbSiO$_3$ | 0.00135 mol (0.38gm) |

The Dean-Stark water separator was filled with 66 ml of decanol-1.

PROCEDURE

With rapid agitation the contents of the flask were heated with a set temperature, regulated by the electronic temperature regulator, of 240° C. After about 1 hour and 15 minutes, the reaction mixture had begun to reflux. After an additional about two hours, the temperature of the reaction mixture had reached 240° C, and was maintained at 240° C for a further 15 minutes. A total of 30 ml of water had distilled over into the Dean-Stark water separator.

The reactor was cooled to 60° C and the contents poured into a steam heated separatory funnel fitted with a thermometer and a mechanical stirrer. The organic phase was washed successively with four 400 ml portions of 6% sodium chloride solution.

The separated organic phase was dried by distillation at 40 mm Hg (water jet aspirator pump) and a maximum pot temperature of 110° C.

The water aspirator was then replaced by a mechanical vacuum pump. All volatile material was distilled off at a maximum pot temperature of 205° C and a vacuum of 1.2 mm Hg. A conversion of decanol-1 of 85% and a yield of 2-octyl dodecanol of 81% were obtained.

EXAMPLE 7

Preparation of 2-hexyldecanol-1

When Example 2 was repeated using 0.38 gm of PbSiO$_3$ in place of 0.70 gm of Basic Silicate White Lead 202 Micronized, and a maximum reaction temperature of 230° C was set, then a conversion of 92% and a yield of 80% of 2-hexyldecanol-1 were obtained. The total time of required heating from the initiation of a steady reflux until 15 minutes after the maximum temperature of 230° C was reached was 190 minutes.

EXAMPLE 8 (COMPARISON)

Example 7 was repeated substituting 0.55 gm of copper powder for the 0.70 gm of Basic Silicate White Lead 202 Micronized. A conversion of 71% and a yield of 89% were obtained. However, the total time of required heating from the initiation of a steady reflux until 15 minutes after the maximum temperature of 230° C was reached was 355 minutes.

EXAMPLE 9 (COMPARISON)

When Example 2 was repeated using 0.6 gm of lead monooxide (PbO) in place of 0.70 gm of Basic Silicate White Lead 202 micronized and the maximum reaction temperature was allowed to reach 235° C, a conversion of 88.4% and a yield of 83% were obtained. The total time of required heating from the initiation of a steady reflux until the maximum temperature was reached was 125 minutes. A noticeable agglomeration of black particles was observed. This could be expected to cause difficulty in commercial usage as it would plug up valves, etc.

EXAMPLE 10 (COMPARISON)

When Example 6 was repeated using 5.0 gm of a lead (+2) ion exchanged Type Y molecular sieve (Linde Molecular Sieve Catalyst Base SK-500) with a maximum reaction temperature of 246° C, a conversion of 75.5% and a yield of 78% were obtained. It was observed that the lead ion exchanged molecular sieve did not maintain its physical integrity, and formed lumps reminiscent of cement, a phenomenon observed with alkali metal silicates are used in a "Guerbet Reaction" system such as the ones described herein.

EXAMPLE 11

Preparation of 2-Benzyl-5-Phenylpentanol-1

When the procedure of Example 6 was applied to the following charge:

3-Phenylpropanol-1 — 2 mols (272 gm)
KOH (45% aqueous solution) — 0.1 mol (12.5 gm)
Basic Silicate White Lead 202 — 0.7 gm, a conversion of 70% and a yield of 72% were obtained.

EXAMPLE 12

Preparation of 2-hexyldecanol-1 using lead titanate

APPARATUS

A 1,000 ml stainless steel resin pot reactor was employed, fitted with a three neck glass top, a glass rod stirrer with teflon blade, an immersed thermometer attached to an electronic temperature regulator and a 65 ml Dean-Stark water separator having a water removal petcock that has a reflux condenser attached to it. Heating was by means of an electrically operated heating mantle. The entire assembly was adequately insulated.

CHARGE

Into the resin pot were charged:
Octanol-1 ("Alfol 8" Conoco Chemicals) — 5.0 mols (650 gm)
KOH (45% aqueous solution) — 0.5 Mols (62.5 gm)
Lead Titanate Powder — 10.0 gm
NL-Industries, Inc. TAM Division (PRODUCT 506)
The Dean-Stark trap was filled with 65 ml of octanol-1.

PROCEDURE

With rapid agitation the contents of the resin flask were heated to a set temperature, regulated by the electronic temperature regulator of 220° C. After 55 minutes, the reflux temperature was 200° C and 54 ml of water had been removed. After an additional 205 minutes, the reaction mixture had reached a temperature of 222° C and a total of 85 ml of water had distilled over into the Dean-Stark trap including that periodically removed from the bottom of the trap.

The reactor was cooled to 60° C and the contents poured into a steam heated separatory funnel fitted with a thermometer and a mechanical stirrer. The organic phase was washed successively with four 1000 ml portions of 6% sodium chloride solution.

The separated organic phase was dried by distillation at 40 mm Hg and a maximum pot temperature of 110° C. 6.5 gm of distillate was recovered.

All volatile material was then distilled over at a maximum pot temperature of 195° C and a vacuum of 4.0 mm Hg. 516 gm of distillate was collected. It showed the following composition by Gas-Liquid Chromatographic Analysis:

| | |
|---|---|
| Octanol-1 | 21.7% |
| Decanol | 0.2% |
| Tetradecanol | 0.7% |
| Unknown | 0.3% |
| Unsaturated $C_{16}$ alcohol | 0.6% |
| 2-Hexyldecanol-1 | 76.3% |

A residue weight of 26 gm was obtained.

These data correspond to an 83.3% conversion of octanol-1 (counting the 20 gm of octanol-1 in the Dean-Stark water separator that flowed back into the reactor) and a yield of 75.84% of 2-hexyldecanol-1 based on reacted octanol-1.

EXAMPLE 13

Preparation of 2-hexyldecanol-1 using Lead zirconate

When the conditions of Example 12 were repeated substituting 2.0 gm of Lead zirconate (N-L TAM PRODUCT 516) for the 10.0 gm Lead titanate, the remainder of the experimental conditions being duplicated, the following results were obtained:

After 100 minutes, the reflux temperature was 200° C and 54 ml of water had been removed. After an additional 195 minutes, the reaction mixture had reached a temperature of 222° C and a total of 82 ml of water had distilled over into the Dean-Stark trap.

After washing and drying, the organic phase was distilled to a pot temperature of 215° C at 1.0 mm Hg. 523 gm of distillate was obtained. It showed the following composition by Gas-Liquid Chromatographic Analysis:

| | |
|---|---|
| Octanol-1 | 13.1% |
| $C_{14}$-Alcohol | 0.5% |
| $C_{16}$-Alcohol | 0.3% |
| 2-Hexyldecanol-1 | 84.6% |
| $C_{24}$-Alcohol | 1.0% |
| $C_{26}$-Alcohol | 0.5% |

A residue weight of 17 gm was obtained. These data correspond to an 89.8% conversion of octanol-1 (counting the 20 gm of octanol-1 in the Dean-Stark water separator that flowed back into the reactor) and a yield of 79.2% of 2-hexyldecanol-1 based on reacted octanol-1.

EXAMPLE 14

Preparation of 2-octyldodecanol-1

APPARATUS

A 500 gallon stainless steel reactor was employed having an oil heated jacket, an agitator, an overhead condenser, a phase separator and a nitrogen sparger.

CHARGE

Into the reactor were charged:
3,400 lbs. n-Decanol, 99%
100 lbs. KOH (45% aqueous solution)
5 lbs. Lead metasilicate

PROCEDURE n-Decanol, KOH solution and lead metasilicate were charged into the reactor at room temperature. With moderate nitrogen sparging and continuous agitation the reaction mixture was then heated gradually in approximately 90 minutes to a temperature of 140° C, at which point water started to collect in the phase separator. The reaction temperature was steadily increased over the next 6 hours to a final reading of 250° C, at which point cooling was applied to the vessel.

During the reaction period, water was from time to time drawn off from the separator, whereas condensed alcohol was continuously refluxed to the reactor. A total of 225 lbs. of water was collected.

After cooling of the reaction mixture to 90° C, the raw product was washed three times with 1000 lbs. of a 1% $Na_2SO_4$ solution each time. The washed product yield was 2,984 lbs.

A sample of the washed product was distilled in laboratory equipment at 2 torr and a final sump temperature of 250° C, yielding 93% distillate and 3.3% residue.

The distillate was analyzed by the Gas-Liquid Chromatographic method, showing the following composition:
16.5% $C_{10}$ — Alcohol
80.8% $C_{20}$ — Alcohol (Guerbet Alcohol)
2.7% $C_{30}$ — Alcohol (Guerbet Alcohol)

EXAMPLE 15

Preparation of 2-hexyldecanol

The apparatus of Example 14 was employed.

CHARGE 3,400 lbs. n-Octanol, 99%
100 lbs. KOH (45% aqueous solution)
10 lbs. lead metasilicate

PROCEDURE n-Octanol, KOH-solution and lead metasilicate were charged into the reactor at room temperature. With moderate nitrogen sparging and continuous agitation, the reaction mixture was then heated gradually in approximately 90 minutes to a temperature of 140° C, at which point water started to collect in the phase separator. The reaction temperature was then steadily increased over the next 10 hours to a final reading of 249° C, at which point cooling was applied to the vessel.

During the reaction period, water was from time to time drawn off from the separator, whereas condensed alcohol was continuously refluxed to the reactor. A total of 319 lbs. of water was collected.

After cooling of the reaction mixture to 90° C, the raw product was washed three times with 1000 lbs. of 1% $Na_2SO_4$ solution each time. The washed product yield was 2,900 lbs.

A sample of the washed product was distilled in laboratory equipment at 2 torr and a final sump temperature of 250° C, yielding 95% distillate and 2.8% residue.

The distillate was analyzed by the Gas-Liquid Chromatographic method, showing the following composition:
9.8% $C_8$ — Alcohol
84.2% $C_{16}$ — Alcohol (Guerbet alcohol)

6.0% $C_{24}$ and higher — Alcohols (Guerbet alcohol)

The proceeding specific embodiments are illustrative of the practice of the invention. It is to be understood, however, that other expedients known to those skilled in the art or disclosed herein may be employed without departing from the spirit of the invention or the scope of the appended claims.

We claim:

1. In the process for the condensation of alcohols by the Guerbet process for the production of branched alcohols having the formula $$R_2-CH_2-CH_2-\underset{\underset{R_1}{|}}{CH}-CH_2OH$$

wherein $R_2$ and $R_1$ are members having from 2 to 20 carbon atoms selected from the group consisting of alkyl, alkenyl, alkynyl, cycloalkyl alkyl, phenylalkyl and alkylphenylalkyl comprising condensing an alcohol having the formula $$R_2 - CH_2 - CH_2OH$$

with an alcohol having the formula $$R_1 - CH_2 - CH_2OH$$

wherein $R_2$ and $R_1$ have the above-assigned values in the presence of an alkali under conditions whereby the water of reaction is removed substantially as fast as it is formed in the presence of a catalyst at temperatures above 100° C to the reflux temperature, and recovering said branched alcohols, the improvement consisting of conducting said condensation in the presence of from 0.05 to 3.0 gm per mol of total alcohol, of an insoluble lead salt of an oxyacid of a group IV element of the Periodic Table having a molecular weight greater than 27 selected from the group consisting of lead silicates, lead titanates, lead zirconates, lead germanates and lead hafnates, as said sole catalyst.

2. The process of claim 1 wherein said insoluble lead salt sole catalyst is employed in an amount of from 0.15 to 1.5 gm per mol of total alcohol.

3. The process of claim 1 wherein said insoluble lead salt sole catalyst is a lead silicate having a ratio of PbO to $SiO_3$ of from 65 to 90% by weight of PbO based on the weight of PbO + $SiO_3$ in the lead silicate.

4. The process of claim 3 wherein the lead silicate is lead metasilicate.

5. The process of claim 3 wherein the lead silicate is basic silicate white lead.

6. The process of claim 3 wherein the lead silicate is dilead orthosilicate.

* * * * *